(12) United States Patent
Zhang

(10) Patent No.: US 8,388,542 B2
(45) Date of Patent: Mar. 5, 2013

(54) SYSTEM FOR CARDIAC PATHOLOGY DETECTION AND CHARACTERIZATION

(75) Inventor: Hongxuan Zhang, Palatine, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 357 days.

(21) Appl. No.: 12/768,772

(22) Filed: Apr. 28, 2010

(65) Prior Publication Data

US 2010/0280396 A1    Nov. 4, 2010

Related U.S. Application Data

(60) Provisional application No. 61/175,157, filed on May 4, 2009.

(51) Int. Cl.
A61B 5/02    (2006.01)
(52) U.S. Cl. .......................... 600/485; 600/483; 600/501
(58) Field of Classification Search .................. 600/485, 600/501, 483
See application file for complete search history.

(56) References Cited

U.S. PATENT DOCUMENTS

| | | | |
|---|---|---|---|
| 4,356,827 A | 11/1982 | Uemura et al. | |
| 4,432,374 A | 2/1984 | Osanai | |
| 4,649,929 A | 3/1987 | Weaver et al. | |
| 5,105,816 A | 4/1992 | Shimura et al. | |
| 5,265,615 A | 11/1993 | Frank et al. | |
| 5,390,679 A | 2/1995 | Martin | |
| 5,392,781 A | 2/1995 | Phillipps et al. | |
| 5,406,952 A * | 4/1995 | Barnes et al. ................. | 600/485 |
| 5,772,600 A | 6/1998 | Kahn et al. | |
| 5,797,850 A | 8/1998 | Archibald et al. | |
| 5,913,826 A | 6/1999 | Blank | |
| 5,931,790 A | 8/1999 | Peel, III | |
| 5,983,162 A | 11/1999 | Huang | |
| 6,007,491 A | 12/1999 | Ling et al. | |
| 6,120,441 A | 9/2000 | Griebel | |
| 6,381,559 B1 | 4/2002 | Huang | |
| 6,454,721 B1 | 9/2002 | deBoisblanc et al. | |
| 6,506,163 B1 | 1/2003 | Farrell et al. | |
| 6,705,990 B1 * | 3/2004 | Gallant et al. ................. | 600/300 |
| 6,736,782 B2 | 5/2004 | Pfeiffer et al. | |
| 6,746,403 B2 | 6/2004 | Kolluri et al. | |
| 6,878,116 B2 | 4/2005 | Su | |
| 6,923,769 B2 | 8/2005 | Nishii et al. | |
| 7,043,293 B1 | 5/2006 | Baura | |
| 7,160,250 B2 | 1/2007 | Lemaire | |
| 7,192,399 B2 * | 3/2007 | Kjellstrom et al. ........... | 600/485 |
| 7,308,319 B2 | 12/2007 | Lovett et al. | |
| 7,458,937 B2 | 12/2008 | Elliott | |
| 7,479,111 B2 | 1/2009 | Zhang et al. | |

(Continued)

OTHER PUBLICATIONS

Zhenwei Lu and Ramakrishna Mukkamala, "Continuous cardiac output monitoring in humans by invasive and noninvasive peripheral blood pressure waveform analysis", J Appl Physiol., vol. 101, pp. 598-608, 2006.

(Continued)

*Primary Examiner* — Navin Natnithithadha
*Assistant Examiner* — Etsub Berhanu
(74) *Attorney, Agent, or Firm* — Alexander J Burke

(57) ABSTRACT

A system for heart performance characterization and abnormality detection includes an interface for receiving an electrical signal comprising a pressure indicative waveform indicating a heart blood pressure of a patient over a heart beat cycle. A timing detector determines multiple different time periods in at least one heart cycle from the pressure indicative waveform. A patient monitor monitors the multiple different time periods and in response to detection of a variation in at least one of the multiple different time periods exceeding a predetermined threshold or range, generates an alert message associated with the variation.

14 Claims, 8 Drawing Sheets

U.S. PATENT DOCUMENTS

| | | |
|---|---|---|
| 2004/0030261 A1 | 2/2004 | Rantala |
| 2005/0096557 A1 | 5/2005 | Vosburgh et al. |
| 2005/0131308 A1* | 6/2005 | Chio et al. .................... 600/490 |
| 2006/0047213 A1* | 3/2006 | Gavriely et al. .............. 600/513 |
| 2006/0106322 A1* | 5/2006 | Arand et al. .................. 600/514 |
| 2006/0167358 A1* | 7/2006 | Karamanoglu et al. ...... 600/485 |
| 2006/0167361 A1* | 7/2006 | Bennett et al. ................ 600/486 |
| 2007/0129636 A1* | 6/2007 | Friedman et al. ............. 600/481 |
| 2008/0039739 A1* | 2/2008 | Buja .............................. 600/549 |
| 2008/0177191 A1* | 7/2008 | Patangay et al. .............. 600/509 |
| 2008/0200775 A1* | 8/2008 | Lynn .............................. 600/301 |
| 2009/0270739 A1* | 10/2009 | Hatib et al. ................... 600/485 |

OTHER PUBLICATIONS

Paula S. McKinley et al, "Deriving heart period variability from blood pressure waveforms", J. Appl Physiol., vol. 95, pp. 1431-1438, 2003.

Jonathan P. Mynard et al., "Accurate Automatic Detection of End-Diastole From Left Ventricular Pressure Using Peak Curvature", IEEE Transactions on Biomedical Engineering, vol. 55, No. 11, pp. 2651-2657, Nov. 2008.

* cited by examiner

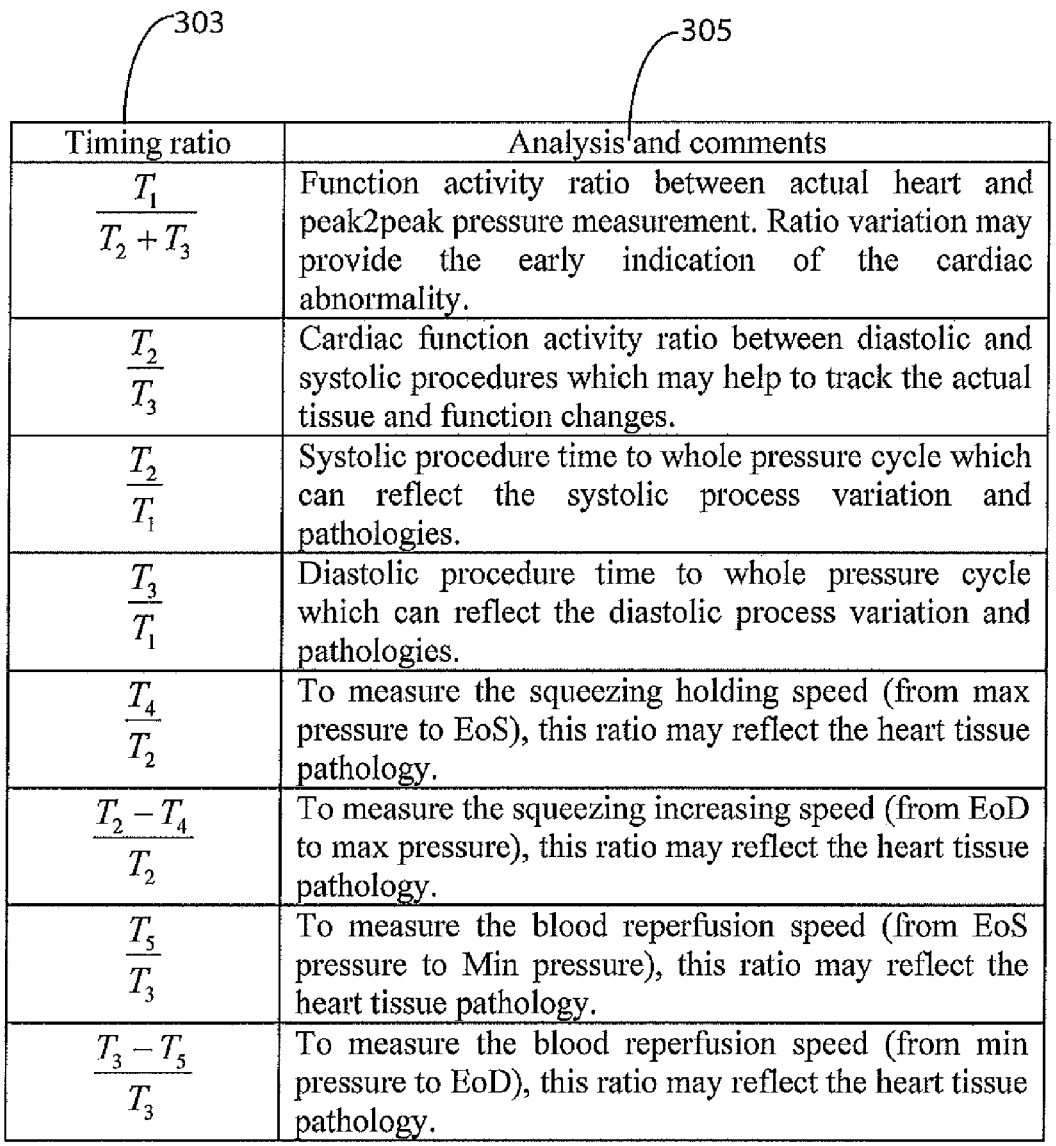

| Timing ratio | Analysis and comments |
|---|---|
| $\dfrac{T_1}{T_2+T_3}$ | Function activity ratio between actual heart and peak2peak pressure measurement. Ratio variation may provide the early indication of the cardiac abnormality. |
| $\dfrac{T_2}{T_3}$ | Cardiac function activity ratio between diastolic and systolic procedures which may help to track the actual tissue and function changes. |
| $\dfrac{T_2}{T_1}$ | Systolic procedure time to whole pressure cycle which can reflect the systolic process variation and pathologies. |
| $\dfrac{T_3}{T_1}$ | Diastolic procedure time to whole pressure cycle which can reflect the diastolic process variation and pathologies. |
| $\dfrac{T_4}{T_2}$ | To measure the squeezing holding speed (from max pressure to EoS), this ratio may reflect the heart tissue pathology. |
| $\dfrac{T_2-T_4}{T_2}$ | To measure the squeezing increasing speed (from EoD to max pressure), this ratio may reflect the heart tissue pathology. |
| $\dfrac{T_5}{T_3}$ | To measure the blood reperfusion speed (from EoS pressure to Min pressure), this ratio may reflect the heart tissue pathology. |
| $\dfrac{T_3-T_5}{T_3}$ | To measure the blood reperfusion speed (from min pressure to EoD), this ratio may reflect the heart tissue pathology. |

FIGURE 4

| | Calculation methods | Analysis and concept |
|---|---|---|
| 407 | $A_{T_1}, A_{T_2}, A_{EoS}, A_{EoD}, A_{T_i}/A_{T_j}$, etc., $Mean(portion_{T_i})$, $Mean(A_{T_i}/A_{T_j})$, $STD(portion_{T_i})$, $STD(A_{T_i}/A_{T_j})$, etc | Absolute value and ratios for each portion of the heart activities, which may include any combination of the two portion signals, such as relative changes. The amplitude calculation includes different kinds of statistical analysis, such as mean value, standard deviation. |
| 409 | $f(portion_{T_i})$, $f(portion_{T_i})/f(portion_{T_j})$, $Mean(f(portion_{T_i}))$, $mean(f(portion_{T_i})/f(portion_{T_j}))$, $STD(f(portion_{T_i}))$, $STD(f(portion_{T_i})/f(portion_{T_j}))$ | Frequency analysis and ratios for each portion of the heart activities, which include different combinations of two portions of signal, such as indicating relative changes. The frequency calculation includes different kinds of statistical analysis, such as mean value, standard deviation. |
| 411 | $\int_{T_i} \alpha \cdot vol(\Delta T_i)$, $\int_{T_i} \alpha \cdot vol(\Delta T_i) / \int_{T_j} \alpha \cdot vol(\Delta T_j)$, $mean(\int_{T_i} \alpha \cdot vol(\Delta T_i))$, $mean(\int_{T_i} \alpha \cdot vol(\Delta T_i) / \int_{T_j} \alpha \cdot vol(\Delta T_j))$, $STD(\int_{T_i} \alpha \cdot vol(\Delta T_i))$, $STD(\int_{T_i} \alpha \cdot vol(\Delta T_i) / \int_{T_j} \alpha \cdot vol(\Delta T_j))$ | In which, $\alpha$ is coefficient between blood volume and pressure integration. Blood volume analysis and ratios for each portion of the heart activities, which include different combinations of the two portion signals, such as relative changes. The blood volume calculation includes different kinds of statistical analysis, such as mean value, standard deviation. |

US 8,388,542 B2

SYSTEM FOR CARDIAC PATHOLOGY DETECTION AND CHARACTERIZATION

This is a non-provisional application of provisional application Ser. No. 61/175,157 filed May 4, 2009, by H. Zhang.

FIELD OF THE INVENTION

This invention concerns a system for heart performance characterization and abnormality detection by determining, and monitoring variation in, different time periods in a pressure indicative waveform over at least one heart cycle.

BACKGROUND OF THE INVENTION

Invasive and non-invasive blood pressure analysis is utilized for heart and cardiac circulation monitoring and function evaluation. Usually blood pressure measurements at different sites (such as left atrial, right atrial sites) as well as a cardiac output calculation are utilized to diagnose and characterize cardiac function and patient health status. Known blood pressure analysis systems fail to comprehensively capture patient health information from pressure monitoring by waveform morphology variation analysis, waveform component analysis and amplitude and frequency variability analysis. Known systems are able to calculate heart period variability (HPV) from a blood pressure waveform for reliable vital sign acquisition and potential analysis of cardiovascular diseases. However, known system lack clinical analysis capability and criteria, for comprehensive qualitative and quantitative analysis and evaluation of a blood pressure signal.

The cardiovascular system includes a pump (the heart), a carrier fluid (blood), a distribution system (arteries), an exchange system (capillary network) and a collection system (venous system). Blood pressure is the driving force that propels blood along the distribution network. Known analysis using blood pressure signals focuses on stroke volume and cardiac output calculation but fails to detect early change and deviation in blood pressure magnitude and ECG signal distortions. Known systems also fail to adequately combine hemodynamic signal analysis (especially of blood pressure signals) and electrophysiological signal analysis. A system according to invention principles addresses these deficiencies and related problems.

SUMMARY OF THE INVENTION

A system for heart performance characterization and abnormality detection includes an interface for receiving an electrical signal comprising a pressure indicative waveform indicating a heart blood pressure of a patient over a heart beat cycle. A timing detector determines multiple different time periods in at least one heart cycle from the pressure indicative waveform. The multiple different time periods comprise at least two of (a) a time interval T1 substantially between successive peaks in the pressure indicative waveform, (b) a time interval T2 substantially comprising a duration of a Systolic period, (c) a time interval T3 substantially comprising a duration of a Diastolic period and (d) a time interval T4 substantially between a pressure peak and a successive end of Systolic point. A patient monitor monitors the multiple different time periods and in response to detection of a variation in at least one of the multiple different time periods exceeding a predetermined threshold or range, generates an alert message associated with the variation.

BRIEF DESCRIPTION OF THE DRAWING

FIG. 3 shows a table summarizing timing ratios determined for pressure waveform diagnosis, according to invention principles.

FIG. 4 shows a table summarizing different calculation methods used for pressure signal analysis including amplitude, frequency and blood volume calculations, according to invention principles.

DETAILED DESCRIPTION OF THE INVENTION

A system improves sensitivity and reliability of blood pressure (hemodynamic) signal measurement by analyzing, quantifying and characterizing a blood pressure signal and by calculating blood pressure parameters including signal magnitude, a frequency component, an energy component, latency and data variability. The system diagnoses cardiac function and health status, identifies cardiac disorders, characterizes pathological severity, predicts life-threatening events and evaluates drug delivery effects by analysis of an invasive or non-invasive blood pressure waveform. The system analyzes invasive and non-invasive hemodynamic signals at multiple anatomical sites using a multi-channel catheter, for example, and maps calculated parameters (such as dP/dt) to medical conditions for clinical and ICD (implantable cardioverter-defibrillator) applications. The system comprehensively captures waveform information from patient blood pressure signals, associated derived blood pressure data and blood pressure time information for identifying cardiac arrhythmias, pressure waveform morphology and variation. The system analyzes pressure waveform morphology and data within an EoD (end of diastolic) to EoS (end of systolic) period and within an EoS to QRS complex period, for example and identifies deviation in heart chamber activity. Usually cardiac malfunctions and arrhythmia affect cardiac tissue early on, advantageously enabling early detection and diagnosis of small changes using hemodynamic signal analysis.

Electrophysiological signals are relatively easily distorted by electrical noise and bio-artifacts, such as power line noise and patient movement whereas hemodynamic signals (such as blood pressure) typically provide better noise immunity and stability in cardiac function analysis. The system employs blood pressure waveform timing variation analysis in combination with analysis of electrophysiological signals, blood pressure signals and oxymetric signals (such as SPO2), for improved medical condition identification using an artificial neural network (ANN), fuzzy system or other system, for example. The analysis involves synchronization of blood pressure signals and extraction of information including time stamps of atrial activity and ventricle activity, for example. The system further performs multi-site blood pressure ratio analysis and calculates time and frequency parameters, energy distribution, waveform ratios, and waveform statistical parameters and comprises an advantageous lead and sensor arrangement for heart and medical applications, such as blood pressure ratio analysis in ICD equipment.

Figure 1:
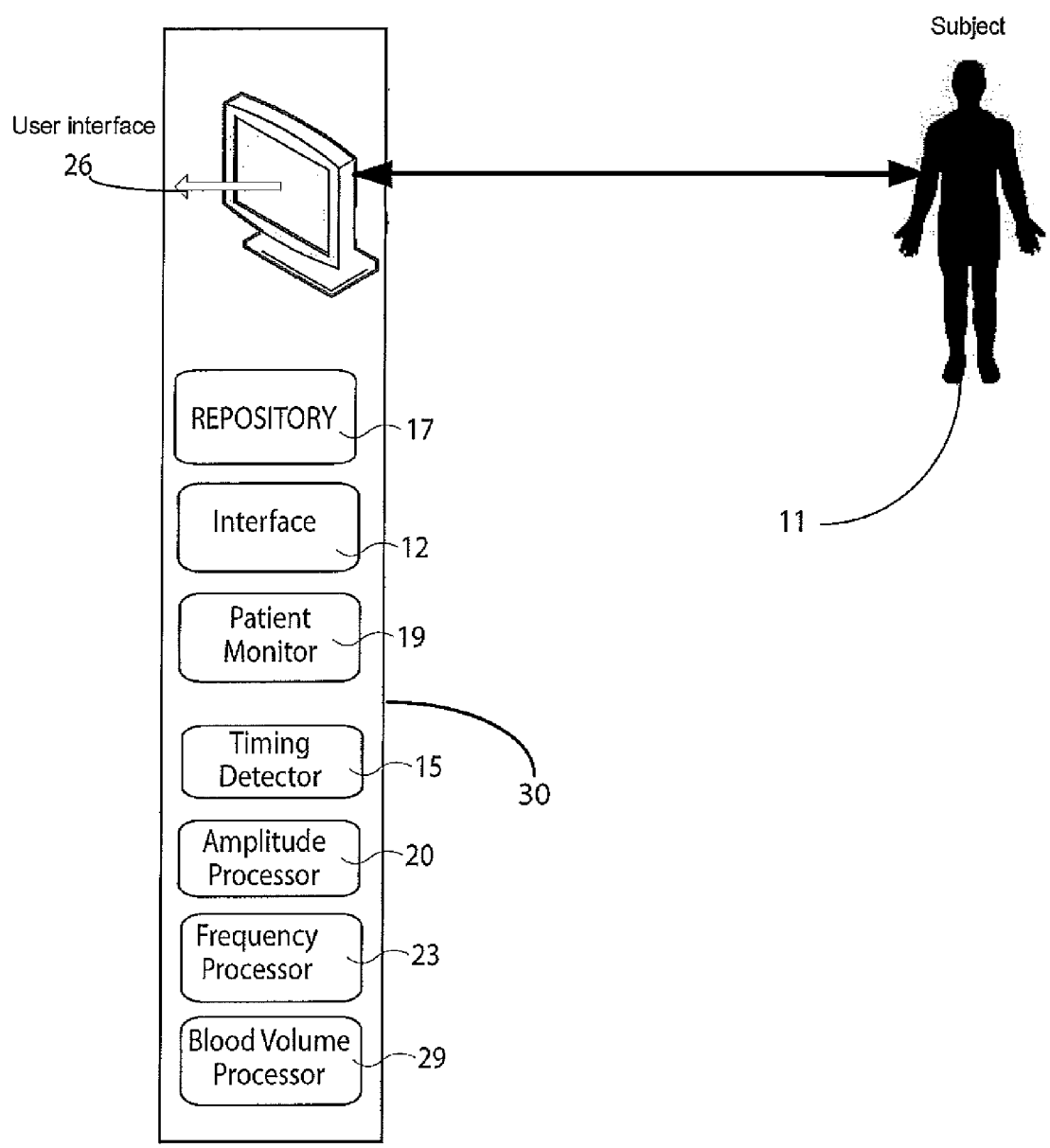
FIG. 1 shows a system for heart performance characterization and abnormality detection, according to invention principles.

FIG. 1 shows system 10 for heart performance characterization and abnormality detection. System 10 analyzes blood pressure signals (hemodynamic signals) and waveform to identify and characterize small changes in heart tissue and functions. For example, in certain disease, one of the heart chambers (such as a left ventricle) fails to work at normal squeezing speed, which may slow down a diastolic time period (affecting parameters including time length, pressure amplitude and rate of pressure change dP/dt). The changes are qualitatively and quantitatively captured using timing analysis, amplitude analysis, frequency analysis, volume analysis and time-frequency analysis to provide computed parameters which provide early warning of impairment of heart functions. The analysis also includes ratio analysis of different portions of the hemodynamic signals and waveform. The system analyzes an individual heart cycle and multiple heart cycles in a pressure signal using timing synchronization and by comparing and averaging parameters of the same particular cycle portion over multiple cycles.

System 10 comprises at least one computer system, workstation, server or other processing device 30 including interface 12, repository 17, patient monitor 19, timing detector 15, amplitude processor 20, frequency processor 23, blood volume processor 29 and a user interface 26. Interface 12 receives an electrical signal comprising a pressure indicative waveform indicating a heart blood pressure of a patient over a heart beat cycle. Timing detector 15 determines multiple different time periods in at least one heart cycle from the pressure indicative waveform. The multiple different time periods comprise at least two of, (a) a time interval T1 substantially between successive peaks in the pressure indicative waveform, (b) a time interval T2 substantially comprising a duration of a Systolic period, (c) a time interval T3 substantially comprising a duration of a Diastolic period and (d) a time interval T4 substantially between a pressure peak and a successive end of Systolic point. Patient monitor 19 monitors the multiple different time periods and in response to detection of a variation in at least one of the multiple different time periods exceeding a predetermined threshold or range, generates an alert message associated with the variation.

Amplitude processor 20 determines multiple different amplitude characteristics in at least one heart cycle of a heart blood pressure indicative waveform. Frequency processor 23 determines multiple different frequency characteristics in at least one heart cycle of a heart blood pressure indicative waveform. Further, blood volume processor 29 determines multiple different blood volume characteristics occurring in at least one heart cycle of a heart blood pressure indicative waveform.

Figure 2:
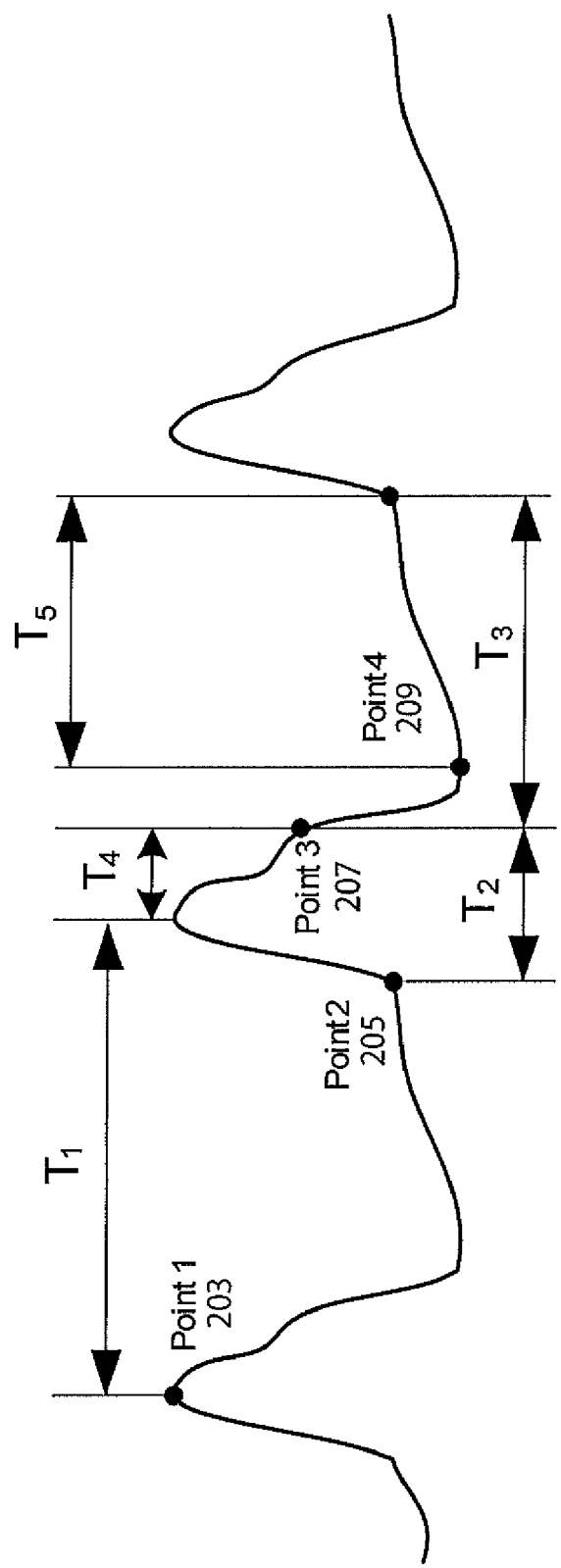
FIG. 2 illustrates a heart pressure signal and waveform and significant timing points, according to invention principles.

FIG. 2 illustrates a heart pressure signal and waveform of one chamber and significant timing points including point 1 (203) maximum pressure time, point 2 (205) end of diastolic (EoD) time, point 3 (207) end of systolic (EoS) time and point 4 (209) minimum pressure time. Points 1, 2, 3 and 4 are detected by known methods such as those described in an article entitled Accurate Automatic Detection of End-Diastole From Left Ventricular Pressure Using Peak Curvature by J. P. Mynard et al., Biomedical Engineering, IEEE Transactions on Volume 55, Issue 11, November 2008 Page(s): 2651-2657. The duration of individual time segments T1, T2, T3, T4 and 15 in the waveform represent the time length of the different heart function procedures, which are used by system 10 to monitor cardiac function. A pressure waveform (over a heart cycle) can be divided into systolic and diastolic portions. System 10 advantageously uses the duration of time portions of FIG. 2 described in Table I and their ratios, to detect small changes in a heart chamber including duration variation and slowing down of a procedure.

TABLE I

| Timing portion | Heart function and status |
|---|---|
| $T_1$ | Pressure signal (peak to peak) based heart cycle length |
| $T_2$ | Systolic time period |
| $T_3$ | Diastolic time period |
| $T_4$ | Max pressure to EoS |
| $T_5$ | Min pressure to EoD |

Blood pressure (BP) is the pressure (force per unit area) exerted by circulating blood on the walls of blood vessels, and constitutes a principal vital sign. The pressure of circulating blood decreases as it moves away from the heart through arteries and capillaries, and toward the heart through veins. For each heartbeat, blood pressure varies between systolic and diastolic pressures. Systolic pressure comprises peak pressure in the arteries, which occurs near the beginning of the cardiac cycle when the ventricles are contracting. Diastolic pressure is minimum pressure in the arteries, which occurs near the end of the cardiac cycle when the ventricles are filled with blood. An example of normal measured values for a resting, healthy adult human is 115 mmHg systolic and 75 mmHg diastolic (written as 115/75 mmHg, and spoken (in the US) as "one fifteen over seventy-five"). Pulse pressure is the difference between systolic and diastolic pressures.

Systolic and diastolic arterial blood pressures are not static but undergo natural variations from one heartbeat to another and throughout the day (in a circadian rhythm). They also change in response to stress, nutritional factors, drugs, disease, exercise, and momentarily from standing up. Sometimes the variations are large. Hypertension refers to arterial pressure being abnormally high, as opposed to hypotension, when it is abnormally low. Along with body temperature, blood pressure measurements are the most commonly measured physiological parameters.

FIG. 3 shows a table summarizing timing ratios determined by system 10 for invasive or non-invasive blood pressure waveform diagnosis. System 10 analyzes blood pressure signals from different chambers in response to user or automatic selection of pressure signal timing ratios from those of column 303, for calculation, for example and also adaptively adjusts associated ratio specific warning thresholds. The calculated ratios include a ratio between maximum to minimum pressure time segment duration, for example. The items of column 305 describe clinical indications associated with the corresponding timing ratios of column 303.

FIG. 4 shows a table summarizing different calculation methods used for pressure signal analysis including amplitude calculations 407, frequency calculations 409 and blood volume calculations 411 for the different time segments T1, T2, T3, T4 and T5 (FIG. 2). The FIG. 4 calculations comprise amplitude, frequency and blood volume ratio calculations for the different time segments and associated mean and standard deviation calculations. The items of column 405 describe clinical indications associated with the corresponding amplitude, frequency and blood volume calculations 407, 409 and 411. System 10 also uses additional processing methods for blood pressure signal analysis including complexity analysis, high order statistical indicator calculation and nonlinear analysis. The different calculations 407, 409 and 411 are used individually and in combination. For example, $A_{EoS}$ and $A_{EoD}$ (Amplitude of End of Systolic and End of Diastolic segments) are used directly for pressure waveform analysis. Further, the derived differential signal $\|A_{EoS}-A_{EoD}\|$ and ratio signal $$\frac{A_{EoS}}{A_{EoD}}$$

are used to evaluate pressure signal variation and cardiac disease related distortion. Furthermore, other analysis methods, such as time-frequency analysis and complexity analysis, are used for pressure signal and morphology diagnosis. These quantitative calculations provide values for monitoring of cardiac function and tissue and to characterize severity of heart abnormality.

Figure 5:
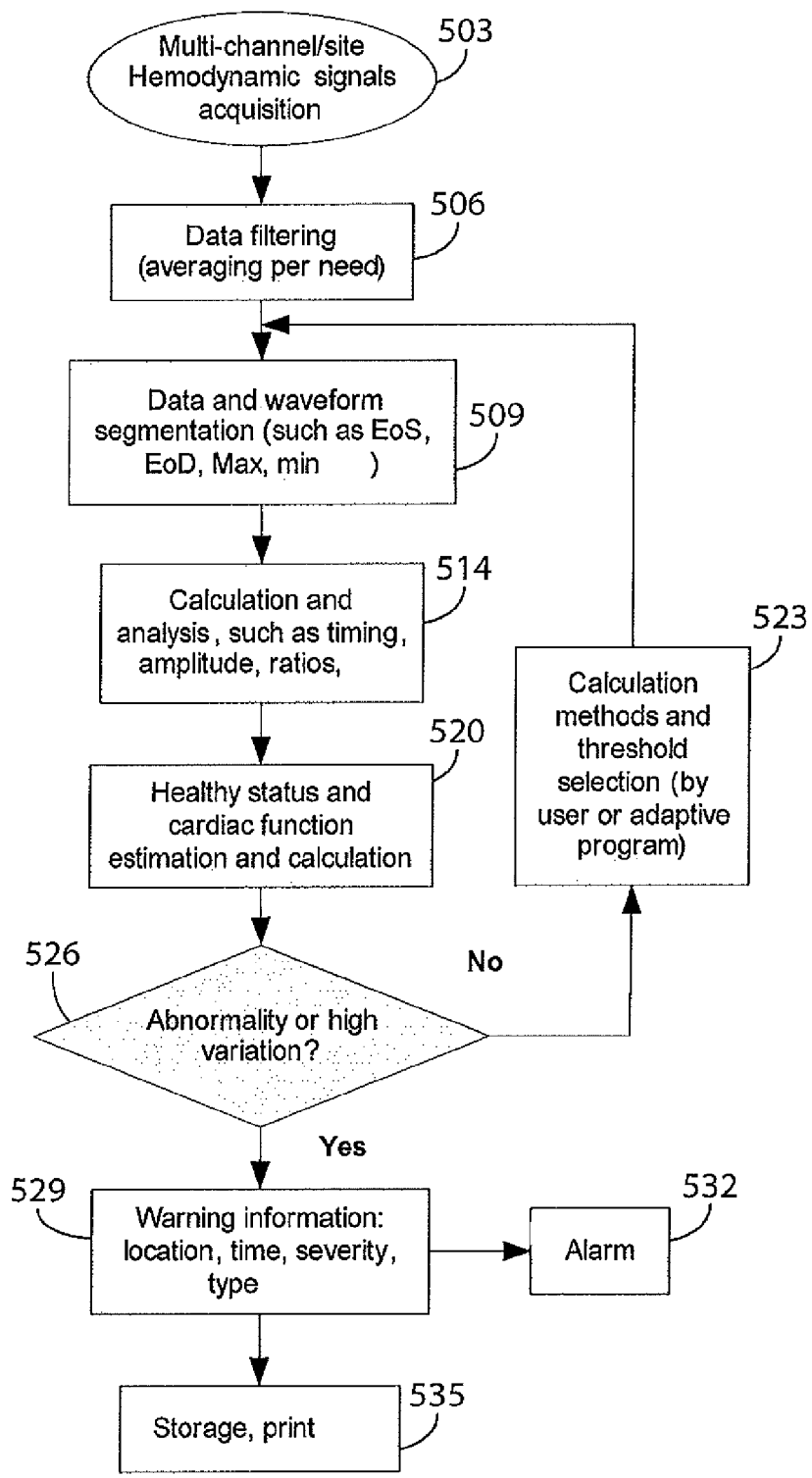
FIG. 5 shows a flowchart of a process for analysis of multi-channel pressure signals to determine location, timing, severity and type of cardiac pathology and disease, according to invention principles.

FIG. 5 shows a flowchart of a process performed by system 10 (FIG. 1) for analysis of multiple catheter channel blood pressure signals to determine location, timing, severity and type of cardiac pathology and disease. Interface 12 in step 503 acquires blood pressure signals from multiple channels of a multi-channel intra-cardiac catheter at multiple cardiac locations. Interface 12 in step 506 filters the acquired blood pressure signals using a filter adaptively selected in response to data indicating clinical application (e.g. ischemia detection, rhythm analysis application). In step 509 timing detector 15 identifies different time segments (maximum, minimum, EOS and EOD time segment, for example) of the filtered blood pressure signals. In step 514, timing detector 15 calculates the timing parameters of FIG. 2 and associated timing ratios of FIG. 3. Amplitude processor 20, frequency processor 23 and blood volume processor 29, calculate amplitude, frequency and blood volume values using the calculations of FIG. 4. Processor 20 determines a baseline signal (e.g. a mean value of the waveform or other value) within a blood pressure waveform for use in determining a threshold for alert generation comparison such as a 10% variation from the baseline, for example.

The threshold may be different for blood pressure signals derived at different anatomical sites including for externally derived pressure, internal ventricular pressure sites and internal atrium pressure sites. Similarly, a threshold tolerance is automatically adjusted based on the environment (such as noise) and clinical application and treatment. Different kinds of signals, such as an electrophysiological signal or vital sign signal (such as ECG, ICEG, SPO2) are used to synchronize the blood pressure signal for analysis, to extract significant signals and time stamps such for atrial activity and ventricle activity. System 10, for example, uses a time interval between an ECG signal R wave to a maximum pressure point, for parameter and ratio analysis for tracking cardiac function. Similarly, system 10 uses an SPO2 signal peak to a blood pressure signal peak time interval or ETO2 signal peak to a blood pressure signal peak (or minimum) for parameter and ratio analysis, for tracking cardiac function.

Patient monitor 19 in step 520 monitors the different time periods and values calculated in step 514. Patient monitor 19 uses predetermined mapping information, associating ranges of the different time periods and values with corresponding medical conditions, in comparing a time period and value with the ranges and generates an alert message indicating a potential medical condition. The predetermined mapping information associates ranges of the different time periods and values with particular patient demographic characteristics and with corresponding medical conditions. Patient monitor 19 uses patient demographic data including at least one of, age weight, gender and height in comparing a time period and value with the ranges and generating an alert message indicating a potential medical condition.

In step 526, in response to detection of a value or variation in at least one of the different time periods or values exceeding a predetermined threshold or range, patient monitor 19 analyzes different channel pressure signals to determine the location, timing, severity, type of cardiac pathology and disease and generates an alert message associated with the value or variation in step 529. The alert message identifies the medical condition and abnormality and communicates the message to a user in step 532 and stores or prints the message and records the identified condition in step 535. If patient monitor 19 in step 526 does not identify any medical condition potentially indicating cardiac impairment, patient monitor 19 in step 523 iteratively repeats the process from step 509 using adaptively adjusted comparison thresholds. System 10 uses the calculated different time periods or values to continuously monitor and quantify cardiac condition to achieve early detection of clinical events.

The system 10 calculated values are used to evaluate and characterize patient health and cardiac function status. Further, in response to data indicating clinical application, a statistical calculation and related hypothesis (such as a T test) are utilized for quantification of the stages of cardiac events including identifying a trend. In one embodiment, system 10 calculates and compares time durations and values derived for different segments (using functions shown in FIGS. 3 and 4) of a fast wave portion and slow wave portion of a blood pressure signal. System 10 compares a ratio indicated in FIGS. 3 and 4 of a blood pressure signal fast wave portion and slow wave portion to improve detection of abnormal waveform distortion and pathology related changes and uses empirical mode decomposing (EMD) and intrinsic mode function (IMF) analysis for fast and slow pressure portion signal analysis. System 10 performs multi-anatomical site pressure monitoring for CCU (critical care unit) and ICU (intensive care unit) patients, who may have a high risk of thrombosis or hemorrhage.

Figure 6:
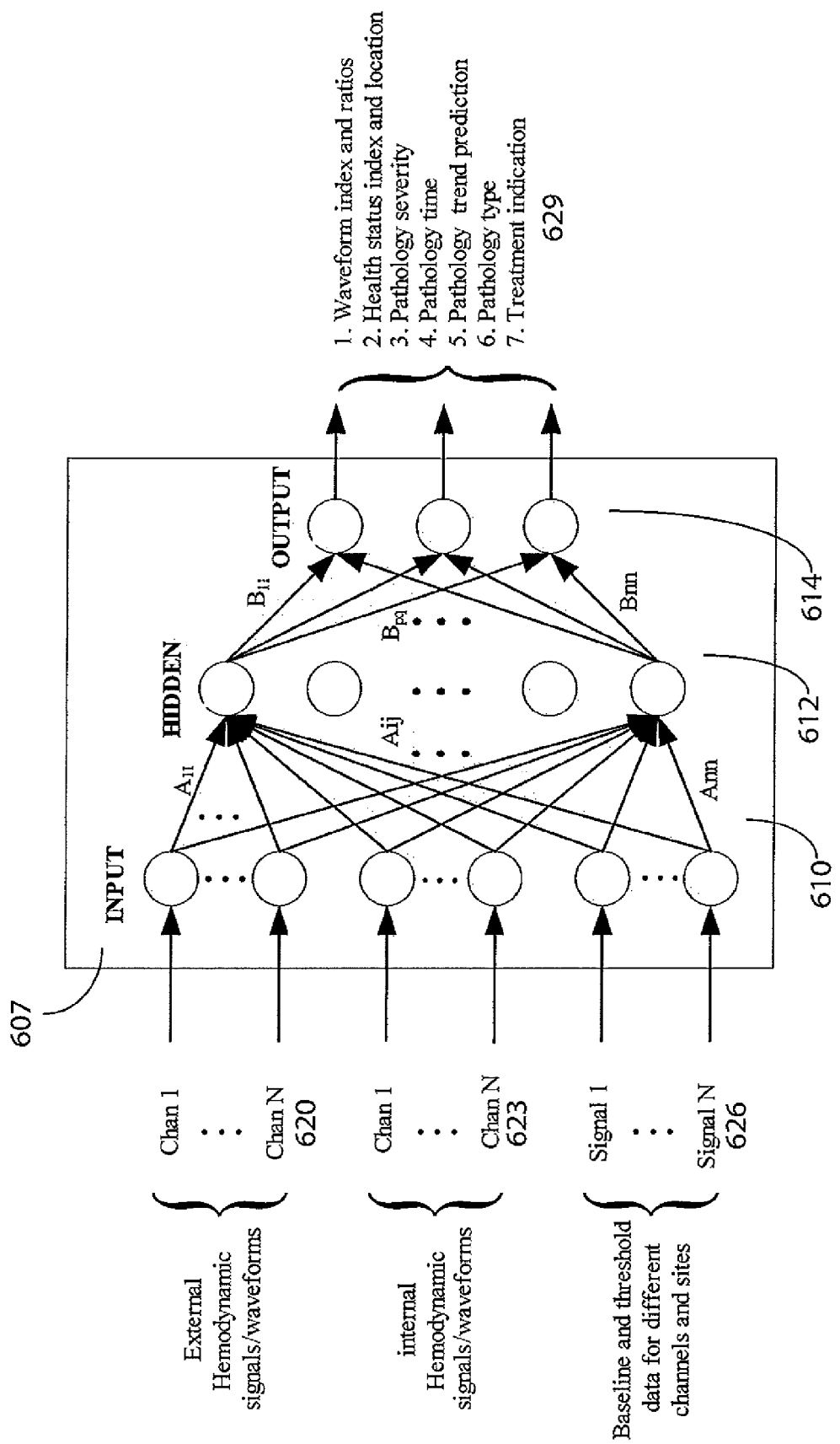
FIG. 6 shows an artificial neural network (ANN) used for heart performance characterization and abnormality detection, according to invention principles.

FIG. 6 shows an artificial neural network (ANN) used by system 10 in one embodiment for heart performance characterization and abnormality detection. ANN unit 607 processes a combination of internal and external multi-site blood pressure signals to identify cardiac disorders. ANN unit 607 maps one or more internal blood pressure signals 623, external blood pressure signals 620 and signal baseline data and alert threshold data for blood pressure signals acquired at different anatomical sites 626, to output parameters 629. Output parameters 629 include blood pressure time segment and related values (as shown in FIGS. 3 and 4), a patient health status index and anatomical location, a pathology severity indicator, a time of a cardiac event, a pathology trend indication, a pathology type indication and candidate treatment suggestions. ANN unit 607 structure comprises 3 layers, an input layer 610, hidden layer 612 and output layer 614. ANN unit $A_{ij}$ weights are applied between input layer 610 and hidden layer 612 components of the ANN computation and $B_{pq}$ weights are applied between hidden layer 612 and calculation index components 614 of the ANN computation. The $A_{ij}$ weights and $B_{pq}$ weights are adaptively adjusted and tuned using a training data set. ANN unit 607 incorporates a selflearning function that processes signals 620, 623 and 626 to increase the accuracy of calculated results.

ANN unit 607 maps input signals 620, 623 and 626 to a candidate diagnosis or treatment suggestion 629 to localize a tissue impairment within an organ and determine time of occurrence within a heart cycle. ANN unit 607 also identifies arrhythmia type (e.g., AF, MI, VT, VF), severity of arrhythmia treatment and urgency level and is usable for automatic heart condition detection, diagnosis, warning and treatment. Further unit 607 performs statistical analysis to construct a threshold used to detect tissue impairment and diagnose and predict cardiac arrhythmia and pathology.

Following a training phase with a training data set, ANN unit 607 maps signals 620, 623 and 626 to data 629 indicating an Arrhythmia type, Arrhythmia severity, candidate treatment suggestions, localized tissue impairment information identifying the cardiac arrhythmia position, pathology conducting sequence, abnormal tissue area and focus of the disorder and irregularity, for example. The severity threshold of a pathology mapping decision may vary from person to person and is adjusted at the beginning of analysis. The system may be advantageously utilized in general patient monitoring and implantable cardiac devices for real time automatic analysis and detection of cardiac arrhythmias and abnormalities. ANN unit 607 is particularly useful in multiple location blood pressure signal pattern analysis, for cross site comparison and to further define arrhythmia type and location.

Figure 7:
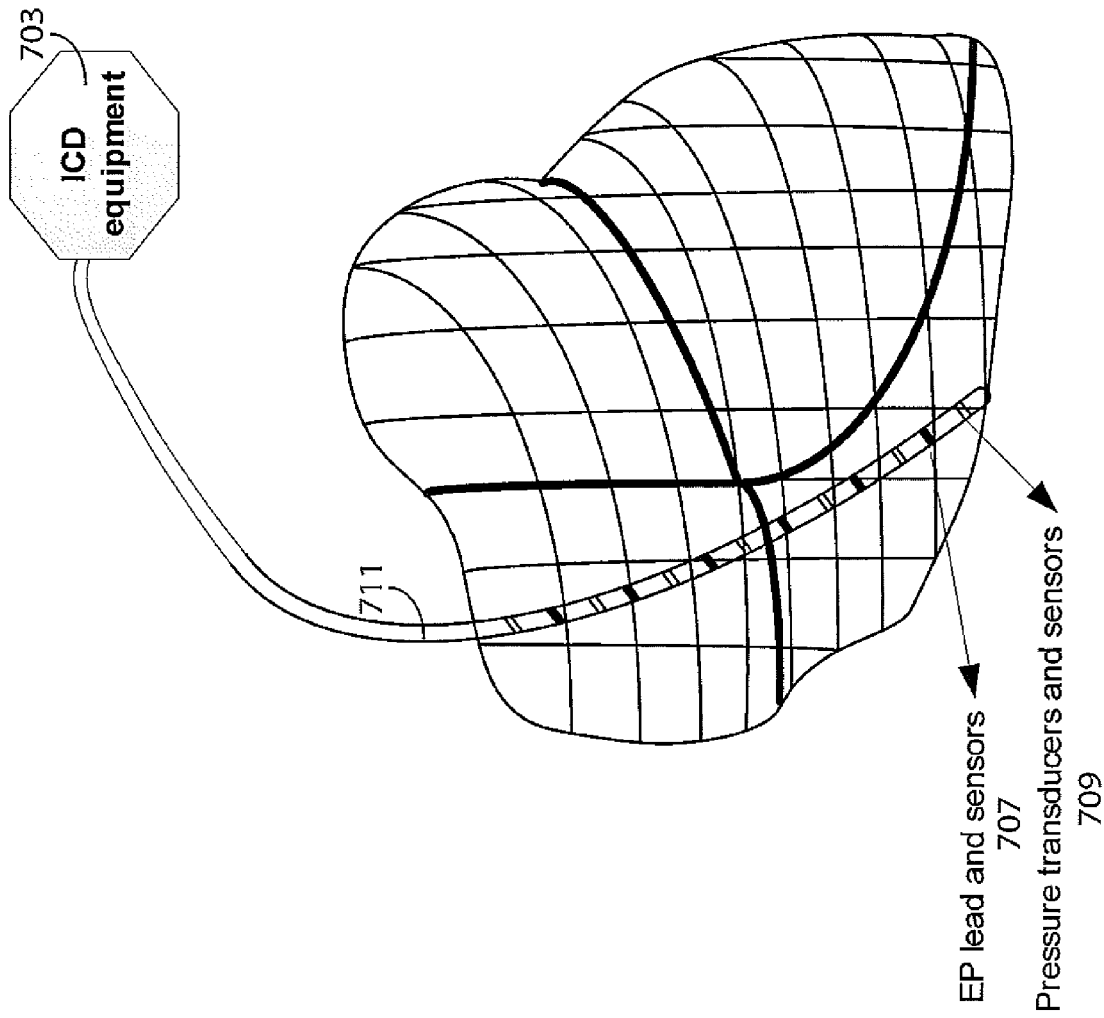
FIG. 7 shows an ICD (implantable cardioverter-defibrillator) system performing blood pressure signal analysis, according to invention principles.

FIG. 7 shows an ICD (implantable cardioverter-defibrillator) system performing multi-site blood pressure signal analysis. System 10 (FIG. 1) performs blood pressure signal analysis to characterize blood pressure signal distortion and variation. ICD monitoring device 703 calculates blood pressure signal time segments and values as shown in FIGS. 3 and 4 for intra-cardiac signal analysis. ICD device 703 is coupled to multi-channel sensors 707 and transducers 709 along catheter 711 providing real time signals, such as EP and pressure signals. Additionally, multi-channel blood pressure signal calculations are performed to determine cardiac status and monitor cardiac functions in 2-dimension and 3-dimension heart mapping. Furthermore, multi-dimensional blood pressure signal value mapping is used in real time for cardiac function diagnosis. System 10 (FIG. 1) uses multi-channel blood pressure signal value mapping to visually indicate abnormal tissue location and arrhythmia severity to a user. The cardiac blood pressure signal analysis is employed in pacemaker and cardiac implantable devices for measurement and characterization of patient cardiac pathology and arrhythmia.

Figure 8:
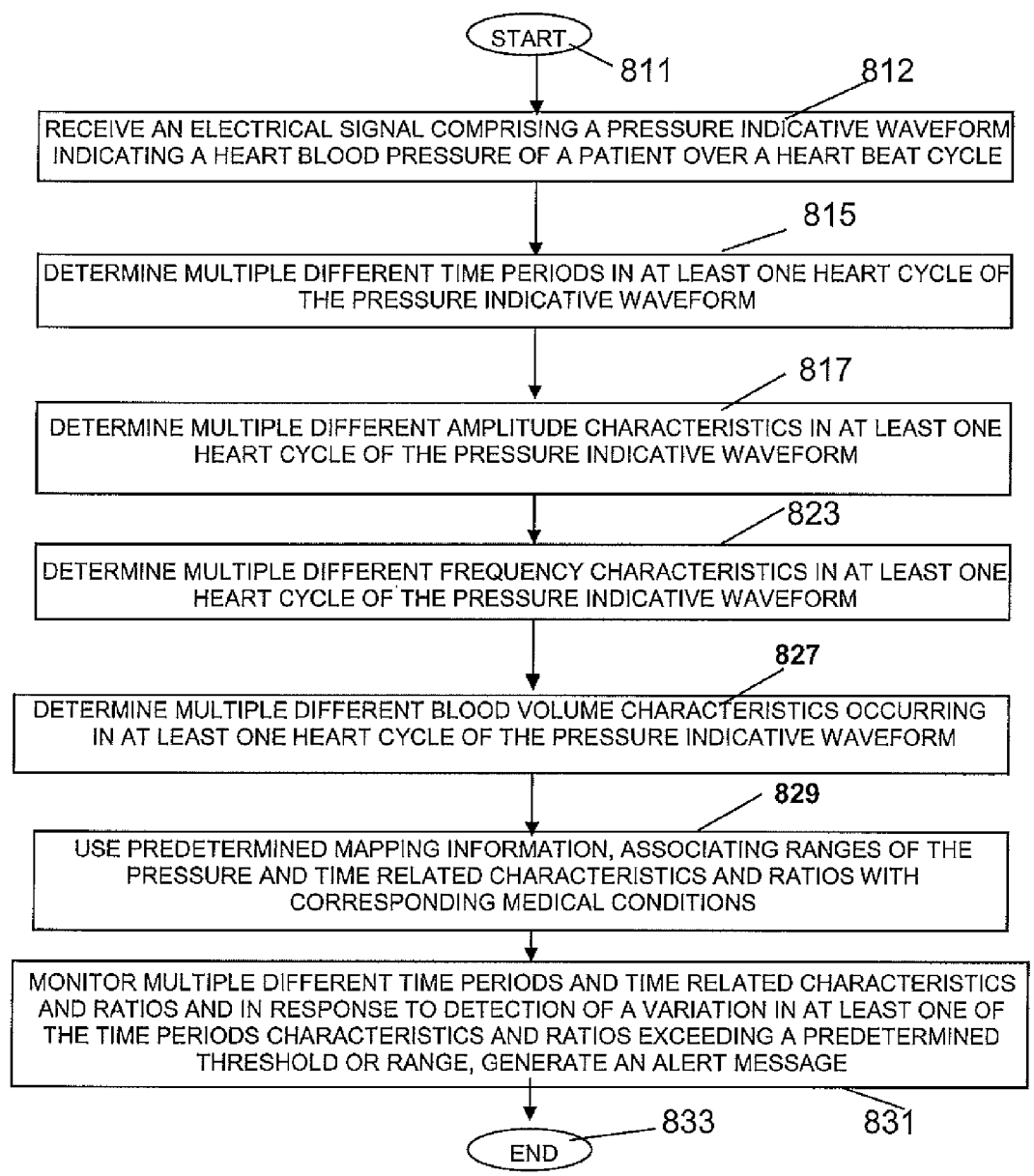
FIG. 8 shows a flowchart of a process used by a system for heart performance characterization and abnormality detection, according to invention principles.

FIG. 8 shows a flowchart of a process used by system 10 for heart performance characterization and abnormality detection. In step 812 following the start at step 811, interface 12 receives an electrical signal comprising a pressure indicative waveform indicating a heart blood pressure of a patient over a heart beat cycle. The electrical signal comprises at least one of, (a) digital data representing the pressure indicative waveform and (b) an analog pressure indicative waveform and is acquired at a particular anatomical location. In step 815, timing detector 15 determines multiple different time periods in at least one heart cycle of the pressure indicative waveform. The multiple different time periods comprise two or more of (a) a time interval T1 substantially between successive peaks in the pressure indicative waveform, (b) a time interval T2 substantially comprising a duration of a Systolic period, (c) a time interval T3 substantially comprising a duration of a Diastolic period, (d) a time interval T4 substantially between a pressure peak and a successive end of Systolic point and (e) a time interval T5 substantially between a pressure minimum point and a successive end of Diastolic point.

In step 817, amplitude processor 20 determines multiple different amplitude characteristics in at least one heart cycle of a heart blood pressure indicative waveform. The multiple different amplitude characteristics substantially comprise at least one of; (i) an amplitude of the pressure indicative waveform occurring in time interval T1, T2, T3 or T4, (ii) an amplitude of the pressure indicative waveform occurring at an end-Diastolic point and (iii) an amplitude of the pressure indicative waveform occurring at an end-systolic point, (iv) a ratio of amplitudes of the pressure indicative waveform occurring in time intervals T1, T2, T3 or T4, (v) a mean of at least one of the multiple different amplitude characteristics and (vi) a standard deviation or variance of at least one of the multiple different amplitude characteristics.

In step 823, frequency processor 23 determines frequency characteristics in at least one heart cycle of a heart blood pressure indicative waveform. The multiple different frequency characteristics substantially comprise at least one of, (i) a frequency of a frequency component of the pressure indicative waveform occurring in time interval T1, T2, T3 or T4, (ii) a ratio of frequencies of frequency components of the pressure indicative waveform occurring in time intervals T1, T2, T3 or T4. A frequency of a frequency component comprises at least one of, a peak frequency, a mean frequency and a minimum frequency. Further, frequency processor 23 determines a mean, standard deviation or variance of at least one of the multiple different frequency characteristics. Patient monitor 19 monitors the mean, standard deviation or variance and in response to detection of the mean, standard deviation or variance exceeding a predetermined threshold, generates an alert message associated with the detected mean, standard deviation or variance.

In step 827, blood volume processor 29 determines multiple different blood volume characteristics occurring in at least one heart cycle of a heart blood pressure indicative waveform. The multiple different blood volume characteristics substantially comprise at least two of, (i) a blood volume characteristic occurring in time interval T1, T2, T3 or T4 of the pressure indicative waveform and (ii) a ratio of blood volumes occurring in a vessel or chamber in time intervals T1, T2, T3 or T4 of the pressure indicative waveform. Blood volume processor 29 determines a mean, standard deviation or variance of at least one of the multiple different blood volume characteristics. Patient monitor 19 monitors the mean, standard deviation or variance and in response to detection of the mean, standard deviation or variance exceeding a predetermined threshold, generates an alert message associated with the detected mean, standard deviation or variance.

In step 829, patient monitor 19 uses predetermined mapping information, associating ranges of different ratios derived using the different time periods and other determined characteristics with corresponding medical conditions. The predetermined mapping information associates ranges of the different ratios and characteristics with particular patient demographic characteristics and with corresponding medical conditions and patient monitor 19 uses patient demographic data including at least one of, age weight, gender and height in comparing a ratio with the ranges. In step 831, patient monitor 19 monitors different time periods, ratios derived using the different time periods and other determined amplitude, frequency and blood volume characteristics. In response to a monitored time period, ratio derived using the different time periods and other determined characteristics or their variation exceeding a predetermined threshold, monitor 19 generates an alert message associated with the ratio.

Patient monitor 19 substantially continuously monitors the multiple different ratios for at least a 24 hour period. The process of FIG. 8 terminates at step 833.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters, A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system analyzes, quantifies and characterizes a blood pressure signal by deriving signal segment time duration, amplitude, frequency and blood volume characteristics and values derived from the characteristics. Further, the processes and applications may, in alternative embodiments, be located on one or more (e.g., distributed) processing devices on a network linking the units of FIG. 1. Any of the functions and steps provided in FIGS. 1-8 may be implemented in hardware, software or a combination of both.

What is claimed is:

1. A system for heart performance characterization and abnormality detection, comprising:
    an interface for receiving an electrical signal comprising a pressure indicative waveform indicating a heart blood pressure of a patient over a heart beat cycle;
    a timing detector for determining a plurality of different time periods in at least one heart cycle of the pressure indicative waveform, said plurality of different time periods comprising a time interval T1 substantially from first to second successive peaks in the pressure indicative waveform, and a further time interval T4 from a pressure peak to a successive end of Systolic point; and
    a patient monitor for monitoring said further time interval T4 and in response to detection of a variation in said further time interval exceeding a predetermined threshold or range, generating an alert message associated with said variation.

2. A system according to claim 1, wherein
said plurality of different time periods include at least one of
    (a) a time interval T2 substantially comprising a duration of a Systolic period and
    (b) a time interval T3 substantially comprising a duration of a Diastolic period and
said patient monitor derives and monitors a plurality of different ratios using said plurality of different time periods comprising at least one of, and $$\frac{T_1}{T_2+T_3} \text{ and} \tag{a}$$

$$\frac{T_4}{T_2}. \tag{b}$$

3. A system according to claim 2, wherein
said patient monitor substantially continuously monitors said plurality of different ratios for at least a 24 hour period.

4. A system according to claim 2, wherein
said patient monitor uses predetermined mapping information, associating ranges of said different ratios with corresponding medical conditions, in comparing a ratio with said ranges and generates an alert message indicating a potential medical condition.

5. A system according to claim 4, wherein
said predetermined mapping information associates ranges of said different ratios with particular patient demographic characteristics and with corresponding medical conditions and said patient monitor uses patient demographic data including at least one of, age, weight, gender and height in comparing a ratio with said ranges and generating an alert message indicating a potential medical condition.

6. A system according to claim 2, wherein
said timing detector determines a time interval T5 substantially from a pressure minimum point to a successive end of Diastolic point and
said plurality of different ratios includes at least one of, (i) $\frac{T_2 - T_4}{T_2}$, (ii) $\frac{T_5}{T_3}$ and (iii) $\frac{T_3 - T_5}{T_3}$.

7. A system according to claim 1, wherein
said patient monitor substantially continuously monitors said plurality of different time periods for at least a 24 hour period.

8. A system according to claim 1, wherein
said electrical signal comprises at least one of, (a) digital data representing said pressure indicative waveform and (b) an analog pressure indicative waveform and
said electrical signal is acquired at a particular anatomical location.

9. A system according to claim 1, wherein
said patient monitor uses predetermined mapping information, associating ranges of said plurality of different time periods with corresponding medical conditions, in comparing a time period with said ranges and generates an alert message indicating a potential medical condition.

10. A system according to claim 9, wherein
said predetermined mapping information associates ranges of said different time periods with particular patient demographic characteristics and with corresponding medical conditions and said patient monitor uses patient demographic data including at least one of, age, weight, gender and height in comparing a time period with said ranges and generating an alert message indicating a potential medical condition.

11. A system according to claim 1, wherein
said plurality of different time periods include at least one of
(a) a time interval T2 substantially comprising a duration of a Systolic period and
(b) a time interval T3 substantially comprising a duration of a Diastolic period and including
an amplitude processor for determining a plurality of different amplitude characteristics in at least one heart cycle of a heart blood pressure indicative waveform, said plurality of different amplitude characteristics substantially comprising at least one of,
(i) an amplitude of said pressure indicative waveform occurring at an end-Diastolic point and
(ii) an amplitude of said pressure indicative waveform occurring at an end-systolic point, and
said patient monitor monitors said plurality of different amplitude characteristics and in response to detection of an amplitude characteristic exceeding a predetermined threshold, generates an alert message associated with the detected amplitude characteristic.

12. A system for heart performance characterization and abnormality detection, comprising:
an interface for receiving an electrical signal comprising a pressure indicative waveform indicating a heart blood pressure of a patient over a heart beat cycle;
a timing detector for determining a plurality of different time periods in at least one heart cycle of the pressure indicative waveform, said plurality of different time periods comprising a time interval T1 substantially from first to second successive peaks in the pressure indicative waveform, and a further time period of at least one of,
(a) a time interval T4 substantially from a pressure peak to a successive end of Systolic point and
(b) a time interval T5 substantially from a pressure minimum point to a successive end of Diastolic point;
a patient monitor for monitoring said further time period and in response to detection of a variation in said further time period exceeding a predetermined threshold or range, generating an alert message associated with said variation; and including
a frequency processor for monitoring a plurality of different frequency characteristics comprising a frequency of a frequency component of a pressure indicative waveform occurring in a particular time interval.

13. A system according to claim 1, wherein
said plurality of different time periods include at least one of
(a) a time interval T2 substantially comprising a duration of a Systolic period and
(b) a time interval T3 substantially comprising a duration of a Diastolic period and including
a blood volume processor for determining a plurality of different blood volume characteristics occurring in at least one heart cycle of a heart blood pressure indicative waveform, said plurality of different blood volume characteristics substantially comprising at least two of,
(i) a blood volume characteristic occurring in time interval T1, T2, T3 or T4 of said pressure indicative waveform and
(ii) a ratio of blood volumes occurring in a vessel or chamber in time intervals T1, T2, T3 or T4 of said pressure indicative waveform; and
said patient monitor monitors said plurality of different blood volume characteristics and in response to detection of a blood volume characteristic exceeding a predetermined threshold, generates an alert message associated with the detected blood volume characteristic.

14. A method for heart performance characterization and abnormality detection, comprising the activities of:
employing an interface, a timing detector and a patient monitor for,
receiving an electrical signal comprising a pressure indicative waveform indicating a heart blood pressure of a patient over a heart beat cycle;
determining a plurality of different time periods in at least one heart cycle of the pressure indicative waveform, said plurality of different time periods comprising a time interval T1 substantially from first to second successive peaks in the pressure indicative waveform and a time interval T4 from a pressure peak to a successive end of Systolic point; and
monitoring said plurality of different time periods and in response to detection of a variation in time interval T4 exceeding a predetermined threshold or range, generating an alert message associated with said variation.

* * * * *